(12) United States Patent
Casimiro et al.

(10) Patent No.: US 10,416,331 B2
(45) Date of Patent: Sep. 17, 2019

(54) TWO-DIMENSIONAL CAPACITIVE SENSOR FOR LOCATING THE PRESENCE OF AN OBJECT AND/OR OF AN INDIVIDUAL

(71) Applicant: BOSTIK SA, La Plaine Saint Denis (FR)

(72) Inventors: Jessie Casimiro, Brie Comte Robert (FR); Philippe Mabire, Courcouronnes (FR); Julien Haffner, Champs sur Marne (FR); Cedric Margo, Orsay (FR); Yacine Oussar, Paris (FR); Stephane Hole, Paris (FR)

(73) Assignee: BOSTIK SA, La Plaine Saint Denis (FR)

( * ) Notice: Subject to any disclaimer, the term of this patent is extended or adjusted under 35 U.S.C. 154(b) by 80 days.

(21) Appl. No.: 15/537,267

(22) PCT Filed: Dec. 16, 2015

(86) PCT No.: PCT/FR2015/053555
§ 371 (c)(1),
(2) Date: Jun. 16, 2017

(87) PCT Pub. No.: WO2016/097611
PCT Pub. Date: Jun. 23, 2016

(65) Prior Publication Data
US 2018/0003847 A1    Jan. 4, 2018

(30) Foreign Application Priority Data
Dec. 19, 2014  (FR) ...................... 14 62909

(51) Int. Cl.
*G01R 27/26* (2006.01)
*G01V 3/08* (2006.01)
(Continued)

(52) U.S. Cl.
CPC .............. *G01V 3/08* (2013.01); *A61B 5/1117* (2013.01); *G01V 3/088* (2013.01); *G08B 21/043* (2013.01);
(Continued)

(58) Field of Classification Search
USPC .................................................. 324/658–690
See application file for complete search history.

(56) References Cited

U.S. PATENT DOCUMENTS 4,571,626 A * 2/1986 Yamada ............ H01L 27/14643
257/291
5,010,772 A    4/1991 Bourland et al.
(Continued)

FOREIGN PATENT DOCUMENTS

DE          202 11 697 U1    9/2002
DE    10 2009 055121 A1    6/2011
(Continued)

OTHER PUBLICATIONS

International Search Report, dated Mar. 7, 2016, from corresponding PCT/FR2015/053555 application.

*Primary Examiner* — Vincent Q Nguyen
(74) *Attorney, Agent, or Firm* — Young & Thompson (57) ABSTRACT

A capacitive sensor for locating the presence of an individual and/or of an object is provided including:
  a first layer including at least one first electrode extending in a first direction;
  a second layer having at least one second electrode extending in a second direction; in which the first direction is different from the second direction, and in which the first layer is electrically insulated from the second layer.

14 Claims, 4 Drawing Sheets

(51) Int. Cl.
 *A61B 5/11* (2006.01)
 *G08B 21/04* (2006.01)
 *H03K 17/955* (2006.01)
 *A61B 5/00* (2006.01)
(52) U.S. Cl.
 CPC ....... *G08B 21/0469* (2013.01); *H03K 17/955* (2013.01); *A61B 5/6889* (2013.01)

(56) References Cited

U.S. PATENT DOCUMENTS

| | | |
|---|---|---|
| 8,266,971 B1 | 9/2012 | Jones |
| 2007/0164632 A1* | 7/2007 | Adachi ................ A61B 8/4483 310/311 |
| 2007/0213943 A1* | 9/2007 | Curry .................. G01M 5/0033 702/42 |
| 2015/0276963 A1 | 10/2015 | Casimiro et al. |

FOREIGN PATENT DOCUMENTS

| | | |
|---|---|---|
| EP | 0 161 895 A2 | 11/1985 |
| FR | 2 956 137 A1 | 8/2011 |
| WO | 2006/130081 A | 12/2006 |
| WO | 2009/050285 A1 | 4/2014 |
| WO | 2014/053719 A1 | 4/2014 |

\* cited by examiner

TWO-DIMENSIONAL CAPACITIVE SENSOR FOR LOCATING THE PRESENCE OF AN OBJECT AND/OR OF AN INDIVIDUAL

TECHNICAL FIELD

The present invention is in the field of detecting the presence of objects or individuals.

One of the objectives of the present invention is to instrument the floor with one or more sensors capable of detecting and locating the presence of an object and/or individual.

The subject of the present invention thus has an advantageous application for detecting and locating the fall of an individual in a room in which the floor is instrumented with such an arrangement of sensors: the present invention is therefore of particular interest in buildings, medical or not, dedicated to the elderly such as for example retirement homes.

Very clearly, other advantageous applications can be conceived in the context of the present invention, in particular:
  in the security field (for example in museums, individual homes, public areas, etc.); or even
  in the automobile field.

BACKGROUND

The conditions of health and hygiene are improving in many countries; a growing life expectancy is a direct consequence of this.

Thus, the average age of the population in Europe is regularly increasing.

Projections for the 2060 timeframe reveal that the percentage of people over 65 should reach over 50% of the total population compared to scarcely 20% currently.

This general aging of the population motivates people involved in healthcare to find solutions to provide independence to the elderly as long as possible and to do so with a minimum assistance.

Among the various challenges raised by this general aging, one of the issues is to establish effective systems for detecting falls.

In fact, every year there are many falls involving a hospitalization because the fall was not detected in time; it should be noted now that the health of an elderly person can worsen very quickly when care after the fall is delayed too long.

In the state-of-the-art, there are several fall detection systems.
  Among these systems are found:
  those which must be carried at all times such as, for example, anti-fall patches, or else
  those which are intrusive such as for example remote monitoring systems with image processing.
  There are other detection systems avoiding the above disadvantages.

To this end, the document WO 2006/130081 proposes a method for detection of a person getting out of bed. The method proposed in that document is particularly suited to old and/or handicapped people.

More specifically, pressure sensors, inserted in polyurethane foam are connected to a monitoring system which triggers an alarm when the pressure is exerted on the sensors.

Nonetheless, this method using pressure sensors is not suited to detecting falls. In fact, with such a method, it is impossible to distinguish a person who is walking from one who is falling.

Document WO 2009/050285 proposes a floor mat instrumented by a system composed of sensors. This system uses capacitance associated with the deformation of an intermediate layer for detecting without distinction the presence of a person or an object.

Just the same, the sensors inserted in this mat are not suited for detecting specifically the load transfers related to the presence of a person or an object.

Although interesting, the various solutions above do not allow a fine detection of someone's fall. Additionally, the installation of the solutions proposed above is very costly, difficult and tedious to implement.

Alternatively, with the incorporation of capacitive sensors into the floor of a room, the presence of people on the surface can be detected non-intrusively by measuring the variation of a physical magnitude.

In fact, a person on the floor is comparable to a local variation of the permittivity or to the presence of a new electrode.

In this context, capacitive sensors are the sensors of choice for detecting people. In fact, the capacitive sensors operate like capacitors and their capacitance varies when an object or individual comes close: this variation of the capacitance serves to determine whether an object or individual is present near the sensor.

The document FR 2,956,137 thus proposes a floor instrumented with such capacitive sensors for presence detection.
  In that document, the floor comprises:
  a sublayer made up of an electrically insulating material and placed on a slab;
  capacitive sensors placed on the sublayer; and
  a bed layer placed on the sublayer, where this bed layer is insulating and covers over the sensors.

According to this document FR 2,956,137, it is indicated as essential for effective detection with capacitive sensors to have a sublayer made up of an electrically insulating material.

In this document, the installation of an instrumented floor with an electrically insulating sublayer is complex and costly.

The document WO 2014/053719 proposes a solution for avoiding such a sublayer. Thus, that document provides for a capacitive sensor comprising a specific disposition of a plurality of electrodes.

More specifically, in that document, the sensor comprises at least three electrodes extending longitudinally in one single direction.

According to a first advantageous characteristic from that document, to allow a finer detection of the fall of an individual or an object on the floor, the electrodes for the sensor are polarized independently of each other.

According to a second advantageous characteristic from that document, the geometry of the electrodes (radius of curvature of the electrodes and ratio of the separation distances) serve to improve the detection precision.

In any case, the advantageous features proposed in the document WO 2014/053719 do not make it possible to locate the precise position of the individual or the object once it is detected.

The Applicant submits that none of the prior art documents proposes a solution with which to detect and locate precisely the presence of an object or an individual on the floor.

OBJECT AND SUMMARY OF THE INVENTION

The present invention aims at improving the situation described above.

One of the objects of the present invention is to remedy the various disadvantages mentioned above by proposing a easy to install sensor with which to locate the presence of an object and/or an individual.

The subject matter of the present invention according to a first aspect thus relates to capacitive sensor for detecting, locating the presence, evaluating the floor surface and/or tracking the activity of an individual and/or an object.

The surface of an individual and/or an object is here comparable to the surface of the floor which is covered by the individual and/or the object on the floor.

More specifically, the sensor according to the invention comprises:
- a first layer comprising at least one electrode, called first electrode, which extends in a first direction, and
- a second layer having at least one electrode, called second electrode, which extends in a second direction.

Advantageously, the first direction is different from the second direction.

In other words, the first electrode extends in one direction which is not identical to the second direction, meaning, which is not parallel or coincident with the second direction in which the second electrode extends.

Advantageously the first layer is electrically insulated from the second layer.

It should be noted here that, in the same way, when the layer comprises more than one electrode, the electrodes from each layer are advantageously electrically insulated from each other.

According to the present invention, the sensor is therefore composed of two layers, which are electrically insulated from each other, and which each comprise at least one electrode.

The electrodes of each layer extend in two spatial directions which are different; in this way it is possible to have a two dimensional sensor for precisely locating the position of an object and/or an individual on the instrumented floor.

Thus, because of this disposition of technical means, characteristic of the present invention, a sensor is laid out:
- which can easily instrument a floor: each of the sensor layers can be directly integrated into one of the parts the floor: bed, smoothing compound, adhesive, floor covering; and
- which is not only able to detect the presence of an object and/or an individual, but also to have a precise estimate of the position and the surface of the object and/or individual detected on the floor;
- which allows tracking the activity of a person.

Preferably, the first and second directions are substantially perpendicular to each other.

With this geometry for the electrodes from the first layer compared to the second layer, the finest location can be obtained.

Advantageously, the first electrode and/or the second electrode have the form of one filament; meaning a monofilament (the electrode is formed from a single electric wire).

Advantageously the first electrode and/or the second electrode have the shape of a layer of filaments.

Advantageously, the first and second layers extend in planes substantially parallel to each other.

In a preferred embodiment, the first and second layers are superimposed.

According to the invention, it is preferable that each electrode of the first and second layers be electrically insulated by a protective sleeve.

Preferably, this protective sleeve is made at least partially of a polymer.

Advantageously, the sleeves can be held together by a support.

The support therefore serves to keep the sleeves in position relative to each other (and therefore the electrodes); this makes it possible to advantageously keep a substantially constant separation distance (e.g. about 25 cm) between the electrodes such that the electrodes of each layer remain substantially parallel to each other.

Optionally, each support has at least one self-adhesive surface.

Advantageously, each support has a perforated or airy structure, as in the case, for example, of a fabric or web of glass.

Such a structure contributes to the mechanical strength of the part of the floor in which the support is integrated.

Optionally, each support comprises a centimeter mesh net.

In a variant, the mesh net is made up at least partially of a material such as for example a material selected among the following materials: fiberglass, polyester, polypropylene, polyethylene or polyamide.

Other materials providing good mechanics could also be considered in connection with the present invention.

In an embodiment, each electrode of the first and second layers is electrically insulated by a protective sleeve with each sleeve surrounding one electrode.

Preferably, for each layer, the mesh net and the electrodes are assembled together by weaving of the warp yarn and weft yarn type, where said warp yarn and weft yarn are formed respectively by the sleeves and the mesh net.

In an advantageous embodiment, the sensor according to the present invention comprises an electronic driving module.

According to the invention, this driving module is configured:
- to independently apply a voltage to each of the electrodes, and
- to measure the electric charges accumulated on each electrode.

In a specific embodiment, the driving module is configured for applying zero voltage on at least one of the electrodes.

Advantageously the voltage applied to the electrodes is variable over time, such that the equivalent voltage for all conductors or dielectrics of large permittivity and large size can be considered as zero, if it does not vary at the same frequency as the voltage applied to the electrodes.

The frequency of variation of the voltage applied to the electrodes is generally between 10 Hz and 10 MHz.

Advantageously, the sensor according to the present invention additionally comprises an information processing module which is configured for detecting, locating the presence, evaluating the surface on the ground and/or following the activity of an individual and/or an object depending on the spatial distribution of the variations of the measured charges for each of said electrodes.

Thus, compared to the document WO 2014/053719 in which measurement phase differences are measured for detecting an object and/or an individual, the present invention for its part allows additionally locating and following the activity of an object and/or individual by analyzing the progression in space of electric charges from each electrode.

When a measurement is made on an electrode, we speak of measurement electrode.

Advantageously, the information processing module is thus configured for analyzing the spatial distribution of the variations of the measured charges for each of the electrodes in order to derive:

information dependent on the coupling to ground of the measurement electrode if the voltage applied to the measurement electrode is not zero; in the remainder of the description we will speak of "self-capacitance" for designating this information; or information independent of the coupling to ground if the voltage applied to the measurement electrode is zero and the voltage applied to one or more other electrodes is not zero; in the remainder the description we will speak of "mutual-capacitance" for designating this information.

By ground, we mean all conductors or dielectrics of large permittivity or large size whose potential is not affected by the voltages applied to one or more arbitrary electrodes of the sensor.

In a specific embodiment, the sensor further comprises a display module comprising a control screen.

This module is coupled to the information processing module for generating an image on the screen representative of the spatial position of the object and/or individual based on the spatial distribution of the variations of the measured charges for each of the electrodes.

The control screen can be remoted to a control center with a computer network for communication of data between the screen and the sensor; with such a screen it is possible for an operator to intervene in case a fall is detected.

Such a control screen is optional; it can be provided that the operator responds simply after triggering an alarm when a fall has been detected, for example.

Thus, the subject matter of the present invention according to a second aspect relates to a floor structure for locating an object and/or an individual.

In the meaning of the present invention, floor is understood here as any system which has a structure comprising in particular a bed (or bed layer), a primary anchoring layer, possibly a watertight barrier, a smoothing compound layer, an adhesive layer, and/or a covering layer.

According to the present invention, the floor structure comprises at least one capacitive sensor as described above.

A system that is particularly simple to install can be obtained by instrumenting the floor with at least one capacitive sensor as described above, where such a floor is suited for locating the presence of an object and/or an individual.

Bu virtue of the present invention, instrumentation of the floor can be considered for inhabited areas which are being renovated or buildings under construction.

The capacitive sensor can be embedded in a protective envelope which can be polymeric.

Preferably, this protective envelope is self-adhesive.

This variant is particularly attractive for implementation of the invention during construction of the building or at least during renovation of the floors. Such an installation is particularly robust.

In an embodiment, the floor structure has a covering layer.

In this embodiment, the capacitive sensor can be integrated directly into this covering layer.

In an alternative embodiment, the sensor can optionally be attached by adhering, directly or indirectly, on at least a portion of the lower surface of the covering layer.

By covering layer, here one can understand, for example and without limitation, a layer such as parquet (floating or not), tile, flexible covering like knitted, tufted pile, woven or flocked carpet, in rolls or tiles, a needled pile floor covering, in rolls or tiles, a homogeneous or heterogeneous polyvinyl chloride floor covering, a polyvinyl chloride based covering on hemp or polyester support or on polyester support with polyvinyl chloride backing, a polyvinyl chloride-based floor covering on foam, a polyvinyl chloride based floor covering with cork based support, an expanded polyvinyl chloride-based floor covering, a polyvinyl chloride-based semi flexible tile, or even a compressed cork tile with polyvinyl chloride based wear layer.

In another embodiment which can be combined with one of the preceding embodiments, the floor structure has a smoothing compound layer.

The sensor can optionally be attached by adhering, directly or indirectly, on at least a portion of the upper surface of the smoothing compound layer.

Preferably, this smoothing compound layer is at least partially made of mortar with an organic or mineral binder base.

In a variant, it is possible that the floor structure have a smoothing compound layer fixed to the covering layer via an adhesive layer. In this case, the capacitive sensor can be immersed at least partially in the adhesive layer.

In a variant, the floor structure has a bed layer and a smoothing compound layer.

In this variant, the sensor is integrated in the smoothing compound layer by pouring of said smoothing compound layer, where said sensor is attached by adhesive on at least a portion of the upper surface of the bed layer.

A smoothing compound layer is then poured over the sensor.

In this variant, the sensor is then integrated in the smoothing compound layer.

Alternatively, it is possible to not have a smoothing compound layer and to directly insert the sensor in the bed layer. This involves having a sufficiently smooth bed layer for the remainder, in particular for laying the covering.

Thus, the floor structure according to the present invention proposes several possible alternatives allowing an instrumentation of the floor for the detection of the presence of an object and/or individual.

Finally, the subject of the present invention involves, according to a third aspect, a manufacturing method for a floor structure such as described above.

According to the invention, the method comprises in particular:

a first step of positioning a first layer comprising at least one first electrode such that the first electrode extends in a first fixed direction, and a second step of positioning a second layer comprising at least one second electrode such that the second electrode extends in a second direction different from the first direction.

According to the invention, the two layers are electrically insulated from each other.

Preferably, during the second step, the second layer is positioned such that the second direction in which the second electrode extends is substantially perpendicular to the first direction in which the first electrode extends.

Because of these various structural and functional features, the subject of the present invention therefore proposes a sensor, simple to install in a room and low cost, which by being deployed in two directions serves to get a precise location of the object and/or individual located in the room. It is then possible to process the information gathered and track the activity of the object and/or individual and establish a representative image of this activity.

DESCRIPTION OF THE APPENDED DRAWINGS

Other features and advantages of the present invention will emerge from the description below, with reference to attached FIGS. 1 to 7, which illustrate various implementation examples free of any limiting nature and in which.

DETAILED DESCRIPTION OF DIFFERENT EXEMPLARY EMBODIMENTS

A capacitive sensor and a floor structure conforming to various advantageous exemplary embodiments of the present invention are now going to be described with reference to FIGS. 1 to 7.

The examples described here are specifically suited for an application of the type detecting and locating a fall of an elderly person in a retirement home type medical area.

Obviously, here it involves an exemplary application which is purely illustrative; as brought up previously, other applications can also be considered within the scope of the present invention.

As a reminder, one of the goals of the present invention is spatially locating, estimating the surface on the floor and tracking the activity of an object and/or an individual near the floor.

One of the other goals of the present invention is also designing a sensor that is easy to install and allows instrumenting a floor.

In the example described here, a design of a capacitive sensor 100 addressing these various problems is thus provided.

More specifically, in this example, the sensor 100 is intended to instrument a floor for locating the presence and determining the surface occupied by an individual and/or an object near the floor.

A capacitive sensor operates as a capacitor: it is known that the capacitance of a capacitive sensor varies when an individual or an object moves towards or away from the sensor.

A well-known application of capacitive sensors is their use as human interface devices on smartphone tactile keyboards.

Here the technical problem consists of using a capacitive sensor inserted in a floor (floor bed, smoothing compound, adhesive or covering) in order to perform presence and/or fall detection, and also localization for subsequent activity tracking.

As previously explained, in the document WO 2014/053719, locating the spatial position and the surface occupied on the floor by an individual in a room is not possible.

Such a location is made possible in the scope of the present invention by making use of two spatial directions.

Figure 1:
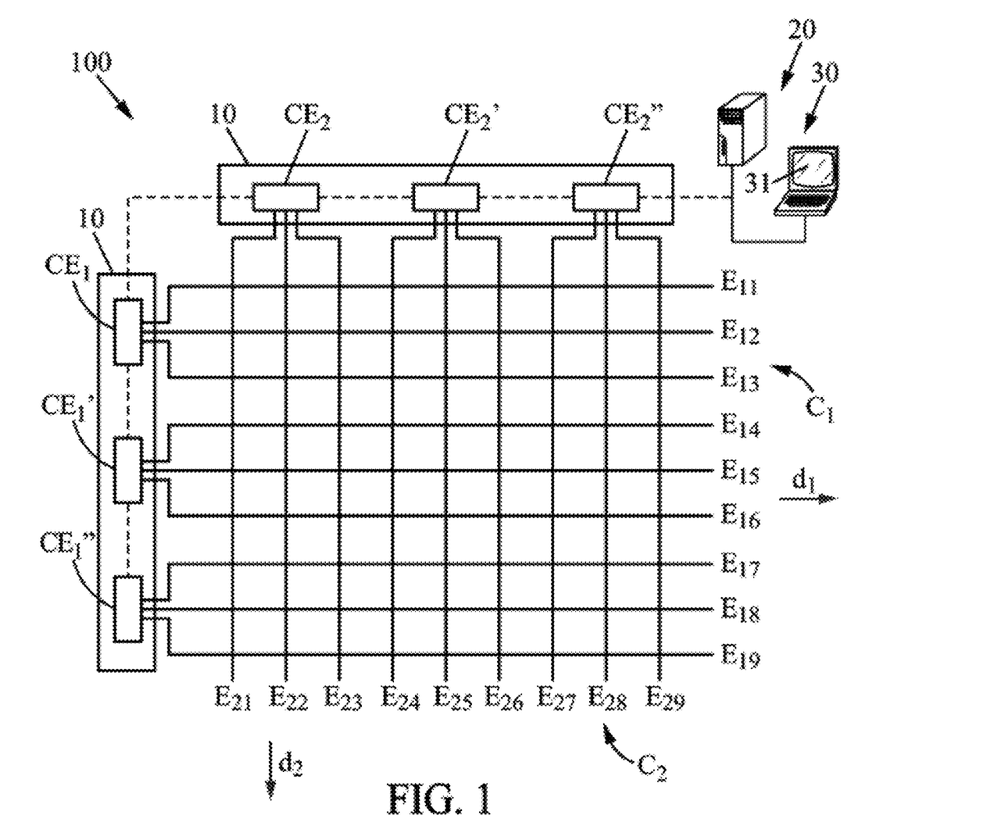
FIG. 1 schematically shows a top view of a capacitive sensor according to an exemplary embodiment of the present invention.
Figure 2:
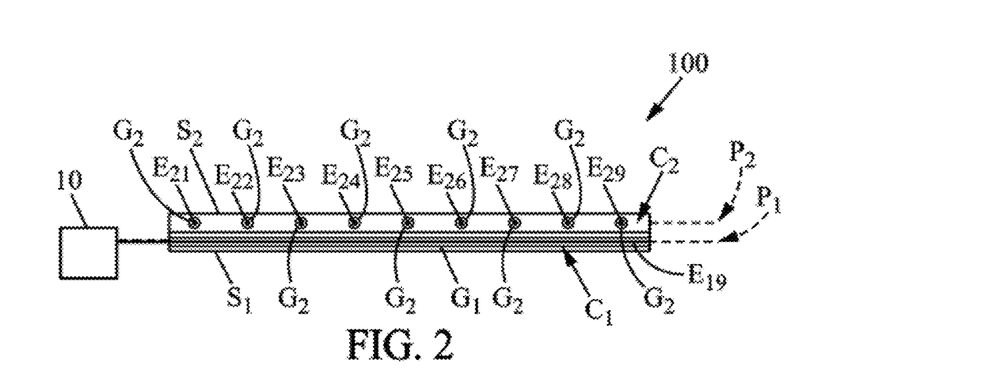
FIG. 2 schematically shows a lateral view of a capacitive sensor according to an exemplary embodiment of the present invention.

In the example described here, and as shown in FIGS. 1 and 2, the sensor 100 thus has a first layer C1 and a second layer C2.

More specifically, in this example, the first layer C1 includes a plurality of electrodes $E_{1i}$, called first electrodes, where the variable i is a positive integer included between 1 and N.

In the example described here and shown in FIG. 1, N is equal to 9. Obviously, this is one example among others.

In the same way, the second layer C2 includes a plurality of electrodes $E_{2j}$, called second electrodes, where the variable j is a positive integer included between 1 and M.

In the example described here and shown in FIG. 1, M is equal to 9. Obviously, this is one example among others.

Here, N is equal to M. This is in no way limiting. It is entirely possible to have other values for these variables; this depends mainly on the dimension of the floor that has to be instrumented.

In this example, the electrodes $E_{1i}$ from the first layer C1 all extend in one direction d1, called first direction; the electrodes $E_{2j}$ from the second layer C2 for their part extend in another direction d2, called second direction.

In the example described, the directions d1 and d2 are mutually perpendicular.

This corresponds to a preferred embodiment with which to get the best precision in the localization. It is however conceivable to have directions which are not mutually perpendicular.

At the least, it is preferable that the directions d1 and d2 are not identical to each other (in other words, they must not be parallel or coincident with each other); the sensor 100 operates correctly when the directions d1 and d2 are oblique to each other.

In the example described here and as shown in FIG. 2, the first C1 and second C2 layers each extend along the respective planes P1 and P2.

While it is not mandatory, it is preferable that these planes P1 and P2 be mutually parallel.

In the example described here, the first and second layers C1, C2 are provided superimposed one against the other. This is desirable for easier laying of the layers C1 and C2.

In the example described here, the layers C1 and C2 are electrically insulated from each other.

To do that, insulating each electrode $E_{1i}$ and $E_{2j}$ in a protective sleeve G1 and G2 is called for; the sleeves are preferably composed at least partially of a polymer.

In the example described here, the sleeves G1, G2 surrounding the electrodes from each layer respectively C1 and C2 are kept together by a support, respectively S1 and S2, such that the electrodes of each layer C1 and C2 remain substantially parallel to each other.

In the example described here, each support S1 and S2 has an airy structure or has perforations.

The supports S1, S2 of the respective layers C1, C2 can be made up of a centimeter mesh net and be self-adhesive.

In the example described here, a net of fiberglass is used to form each support S1, S2; this provides a good integration of each layer C1, C2 into the floor.

Figure 6:
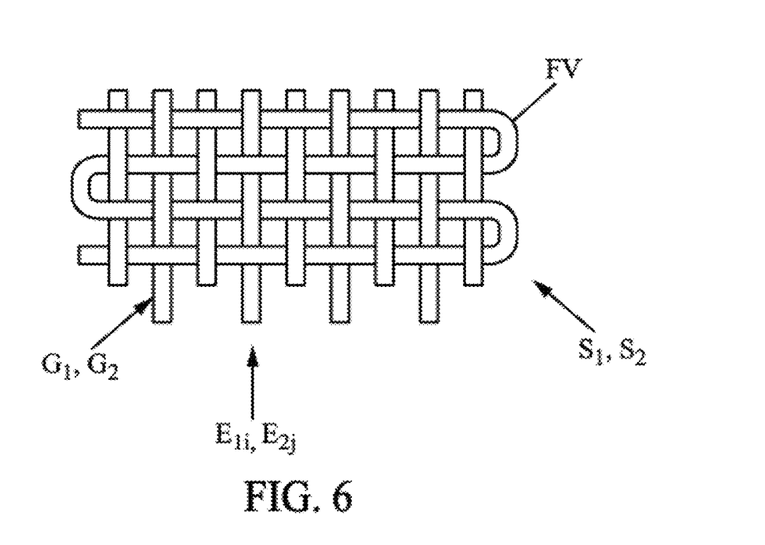
FIG. 6 shows a schematic view of a layer of electrodes for a sensor assembled to each other by weaving with a glass fiber.

In a specific exemplary embodiment shown in FIG. 6, the electrodes from each layer are assembled to each other by weaving, for example by a weft yarn and warp yarn type weaving.

In this example, the sleeves G1 and G2 surrounding the electrodes from each layer C1, C2 form the warp yarn and the fiberglass from the net forms the weft yarn.

Figure 7:
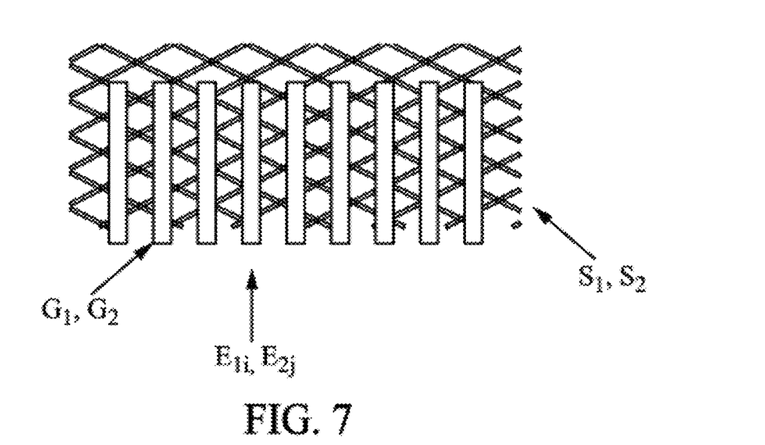
FIG. 7 shows a schematic view of a layer of electrodes for a sensor adhered on wire mesh.

In the exemplary embodiment shown in FIG. 7, the sleeves G1, G2 surrounding the electrodes from each layer C1 and C2 are adhered directly to the support, for example to the centimeter mesh net (or grid).

The sensor 100 according to the exemplary embodiment described here and shown in FIGS. 1 and 2 is particularly effective for establishing a spatial localization of an object and/or an individual and also an estimate of the surface on the floor that it uses.

In fact, each electrode $E_{1i}$ and $E_{2j}$ of the sensor 100 is connected to electronics located outside the floor.

The electronics are made up in particular of electronic driving module 10 itself connected to an information processing module 20.

Such electronic circuitry allows the synchronous driving of the electrodes and the acquisition of electric charge measurements from each electrode.

More specifically, in this example, the module 10 is composed of a plurality of electronic cards CE1, CE1', CE1", CE2, CE2' and CE2".

Here, each card CE1, CE1', CE1", CE2, CE2' and CE2" is connected to a set of three electrodes from a single layer C1 or C2.

In this example, and as shown here in FIG. 1, the card CE1 is therefore connected to the electrodes $E_{11}$, $E_{12}$ and $E_{13}$ of the first layer C1, the card CE1' is connected to the electrodes $E_{14}$, $E_{15}$ and $E_{16}$ of the first layer C1, and so on.

Preferably, the connections between the electrodes $E_{1i}$ and $E_{2j}$ and the electronic measurement cards CE1, CE1', CE1", CE2, CE2' and CE2" are done on the outside (meaning outside the floor), so as to be able to easily repair a defective connection.

A single electronic card can therefore be used to drive and measure independently the capacitance of one or more electrodes $E_{1i}$ and $E_{2j}$.

In the example described here, the cards CE1, CE1', CE1", CE2, CE2' and CE2" are connected to a network, through which they can communicate with each other to have synchronized driving.

With this interconnection, they can also communicate with an information processing module 20 which is away from the instrumented room.

This information processing module 20 contains a program which analyzes and interprets the measurement data sent by each of the cards CE1, CE1', CE1", CE2, CE2' and CE2" of the electronic driving module 10.

The localization can be done via several possible approaches.

According to a first approach, module 10 is configured to measure the charges which depend on the coupling of each electrode $E_{1i}$ and $E_{2j}$ to ground.

In this approach, the electronic driving module 10 is thus configured so that the cards CE1, CE1', CE1", CE2, CE2' and CE2" simultaneously apply the same voltage V to all the electrodes $E_{1i}$ and $E_{2j}$ so as to principally measure the coupling to ground of each electrode $E_{1i}$ and $E_{2j}$.

The presence of an individual near an electrode varies the coupling of this electrode to ground.

It is then possible to locate an individual in the room, based on the position of the electrodes whose charges change and estimate the surface on the floor of said individual depending on the number of electrodes.

For this purpose, the sensor 100 comprises an information processing module 20 which is connected to each of the cards CE1, CE1', CE1", CE2, CE2' and CE2" of the electronic driving module 10 for receiving and processing information about the capacitance variations of each of the electrodes.

More specifically, for estimating the position of the individual in the room and the surface that it occupies on the floor, the processing module 20 identifies the intersections between the rows and columns for which the self-capacitance exceeded a predefined threshold.

With this processing, a spatial position and the surface on the floor of the individual can be estimated.

Several applications can be conceived. For example, a person lying on the floor changes the capacitance of a large number of electrodes.

The sensor 100 can then be used for monitoring elderly people and sending an alert if a fall is detected.

It is observed that, according to this approach, when several "intersections" between the electrodes are touched at the same time, the precision for locating the touched points is limited.

In fact, the electrodes $E_{1i}$ and $E_{2j}$ of the sensor 100 form a grid with the rows for the electrodes $E_{1i}$ from the first layer C1 and the columns for the electrodes $E_{2j}$ from the second layer C2.

Thus, in this example, the sensor 100 has information only on the rows and the columns which were touched.

The intersections which were not in fact touched are nevertheless going to be considered as touched.

Figure 4:
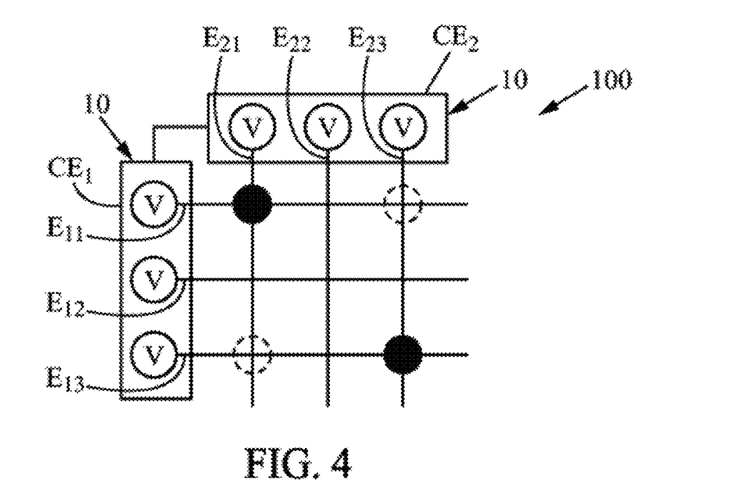
FIG. 4 shows a schematic view of the driving of a sensor according to a first exemplary embodiment.

For example, as shown in FIG. 4, when an individual is effectively near two different intersections (dark spots on FIG. 4), the sensor 100 will spontaneously consider here that four intersections were touched which generates two false points (here the two dashed points on FIG. 4).

For subsequently tracking the activity of the individual and limiting the processing time, the scanning considers only the couplings to ground which are located near the first estimated point (within a radius of 1 m for example).

The activity of the person can be tracked this way; in fact, this step of 1 m correspond substantially to the length of the step of an individual.

The Applicant further submits that the phenomenon of detection of "false touches" inherent in the measurement of the self-capacitances can be considered as negligible in the application which is done here for the detection and location of a fall.

In fact, the position of a standing individual can be estimated with satisfactory precision to be able to follow their movement.

This approach is therefore relevant: the location is sufficiently precise and the calculation time very short. This approach can be preferred for example in rooms where the number of people is small, for example an individual room in a retirement home.

To overcome the phenomenon of detection of "false touches" stated above, a second approach can also be proposed in the scope of the present invention.

This approach rests on the measurement of couplings between electrodes independent of the coupling to ground.

The couplings between electrodes of a sensor correspond to the capacitances at each intersection between the electrodes $E_{1i}$ and $E_{2j}$ of the first layer C1 and the second layer C2.

To measure a capacitance at the intersection of two electrodes, the driving module 10 is then configured such that the electronic cards apply an electric potential to a single electrode and the other electrodes are all grounded.

Figure 5:
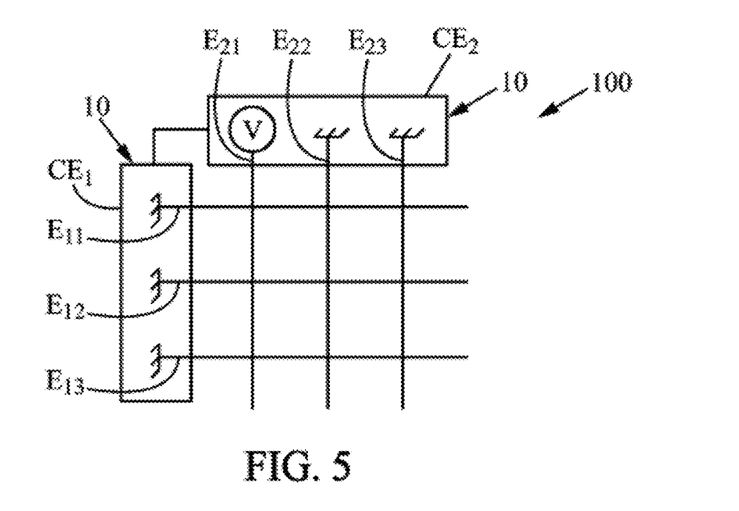
FIG. 5 shows a schematic view of the driving of a sensor according to a second exemplary embodiment.

This is shown in FIG. 5.

Thus, when an individual is located near the intersection of two electrodes (one grounded and one with an applied potential), the variation of the capacitance is obtained by measuring the charges on the grounded electrode.

When the sensor 100 has N electrodes in each direction, a full scan of the capacitances at the intersections then requires N measurements, by applying a voltage to a single electrode each time and by setting all the other sensors to ground.

When the first column (here meaning the electrode $E_{2l}$ of the second layer C2) is the only one to which a voltage is applied (as shown in FIG. 5), the set of mutual-capacitances of the first column with each row is obtained by the measurement on all the rows (here meaning the electrodes $E_{1i}$ of the first layer C1).

This operation must then be repeated N times by changing the polarized electrode each time.

According the approach developed here, the point is measuring the mutual-capacitances for which a variation of coupling to ground was detected, not measuring all of the mutual-capacitances of the sensor 100.

Thus, according to this approach, the coupling to ground of each of the electrodes of the sensor is first measured.

The processing module 20 then processes the information on these couplings to ground in order to select those which are relevant: the processing module 20 is thus configured such that, when one or more rows or columns have a coupling to ground for which the value exceeds a first predefined threshold, then, in this case, the processing module 20 indicates to the driver module 10 to measure the mutual-capacitances at the corresponding crossings of each row and each column.

Thus, according to this approach, not all the mutual-capacitances are measured.

After these new measurements, the mutual-capacitances whose value exceeds a set threshold are then considered as being "activated", meaning that an individual (or an object) is considered as being present above the crossings corresponding to the two electrodes.

According this approach, the processing next continues by measuring only the mutual-capacitances near the area where the individual is located.

In a preferred embodiment, the processing continues solely for the mutual-capacitances in a radius of 1 m around the estimated location, which corresponds approximately to the length of a human step.

It is thus possible to follow the activity of the person with significant precision.

If, for example, the "activated" mutual-capacitances remain the same, that means that the individual remains immobile.

If the nearby "activated" mutual-capacitances change location, it can be concluded that the individual moved.

It is also possible detect a fall on the ground in the case where a large number of nearby crossings are activated simultaneously.

Observe that here this second approach allows a precise localization, in particular when several mutual-capacitances vary at the same time. It is then possible according to this approach to distinguish several people walking in a single room.

Whichever approach is selected, the processing module 20 is configured to incorporate all code instructions with which to manage and process the information so as to perform the localization.

This processing module can next engage with a display module 30 for managing a representative image of the activity of the individual in the room on the control screen 31.

Also observe that, because of the structure thereof, the sensor 100 can be easily integrated in a floor.

Various floor structures 200 are thus conceivable in the scope of the present invention, each of these structures comprising a sensor 100 such as described above.

Figure 3A:
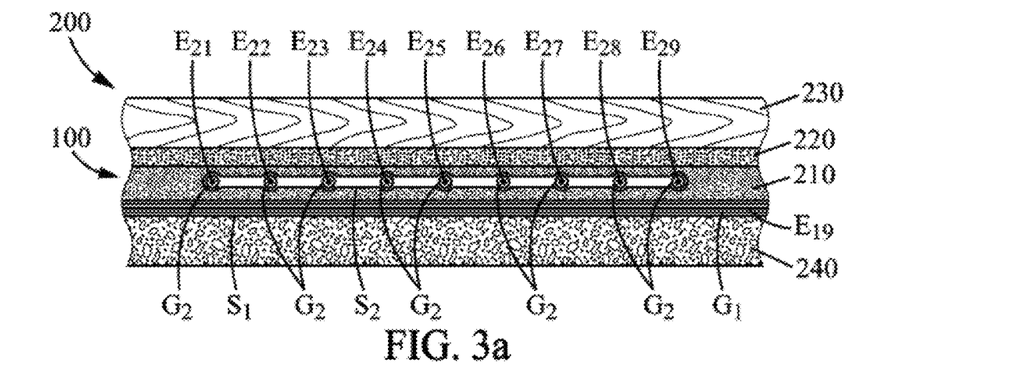
FIGS. 3a to 3c each represent one schematic section view of a floor structure conforming to several exemplary embodiments of the present invention.

Thus, the exemplary embodiment from FIG. 3a calls for the incorporation of a sensor 100 in a smoothing compound layer 210. In this example, in order to provide an easy implementation for laying it, each of the first and second layers C1, C2 of the sensor 100 is immersed in a sleeve G1, G2 in order to electrically isolate each electrode.

In this embodiment, the instrumentation for the floor can, for example, be done in the following way:

placing the bed 240;

applying a primary bonding layer on the bed 240;

first placement step in which the support S1 containing the first layer C1 is positioned such that the first electrodes $E_{1i}$ in this layer C1 extend in a set first direction d1;

second placement step in which the support S2 for the second layer C2 is positioned such that the second electrodes $E_{2j}$ in this layer C2 extend in a second direction d2 which is perpendicular to the first direction d1.

pouring a smoothing compound layer 210 on the layers C1 and C2 of the sensor 100;

applying an adhesive layer 220 and a covering layer 230 on the dry smoothing compound 210 instrumented with sensors 100.

In that way, people near the floor can be detected and located effectively and precisely with a floor instrumented with the capacitive sensor 100 according to the invention.

Figure 3B:
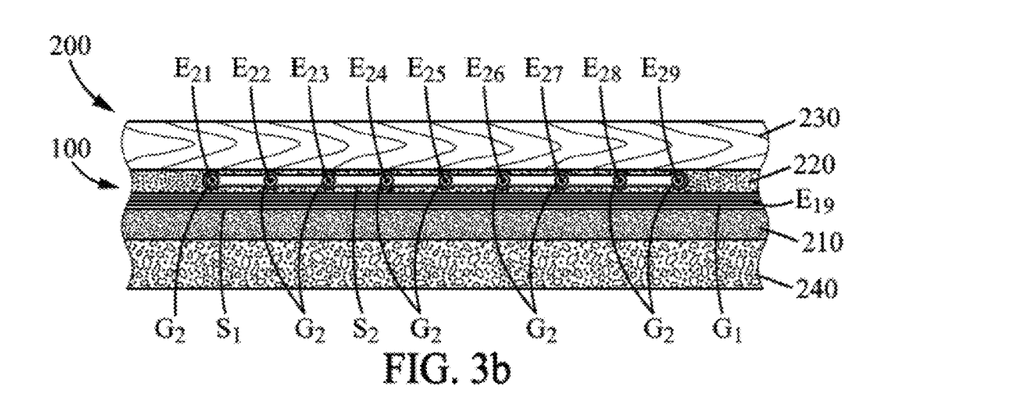

The implementation example from FIG. 3B provides for an instrumentation of the floor with the sensor 100 placed directly or indirectly over the smoothing compound layer 210.

In this example, the instrumentation of the floor is done in the following way: the supports S1 and S2 for the layers C1 and C2 of the sensor 100 are placed one after the other on the smoothing compound 210. A layer of adhesive 220 is next applied on the support S1 and S2, and then a layer of covering 230 is applied on this layer of adhesive 220.

Alternatively, the supports S1 and S2 can be attached on the covering 230 by a layer of adhesive 220, and then the covering 230 on which the supports S1 and S2 are attached is placed on the smoothing compound layer.

Figure 3C:
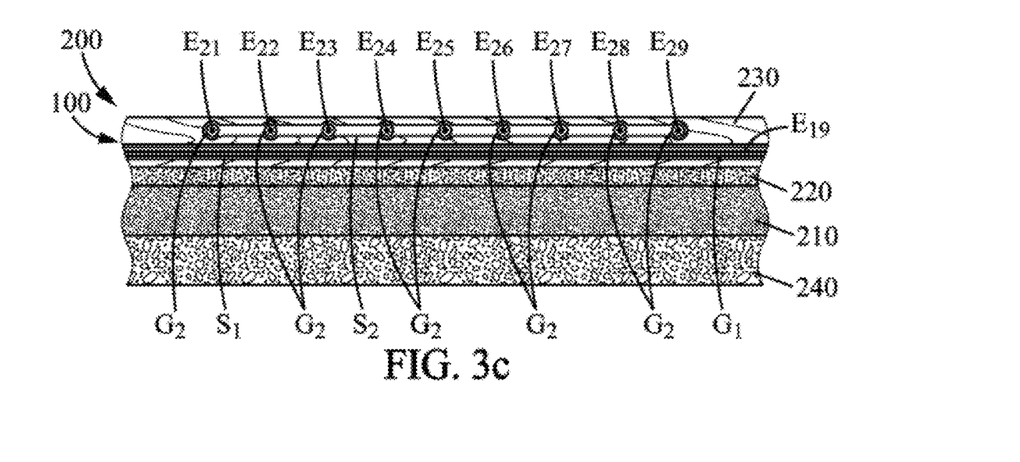

According to another exemplary embodiment shown in FIG. 3c, the sensor 100 is directly inserted in the covering layer 230.

In this example, the preceding installation steps are handled by having previously fabricated a covering layer 230 and instrumented (for example by weaving) the sensor 100 with the floor covering 230.

Thus, the structure of the sensor as provided in the scope of the present invention, with two layers of electrodes electrically insulated from each other, is particularly advantageous and allows the design of a capacitive sensor 100 guaranteeing a fine and precise localization of individuals and/or objects which are located near said sensor.

The resulting sensor 100 according to the present invention can easily serve to instrument a floor for an application for example in medical buildings and or retirement homes.

It should be observed that the present detailed description contains specific implementation examples for the present invention, but in no case does this description have a limiting nature of any kind on the subject matter of the invention; quite the opposite, its goal is to remove any possible imprecision or misinterpretation of the following claims.

The invention claimed is:

1. A capacitive sensor for detecting, locating a presence, evaluating a floor surface and/or tracking an activity of an individual and/or an object,
    said sensor comprising:
        a first layer comprising at least one first electrode extending in a first direction; and
        a second layer having at least one second electrode extending in a second direction;
        wherein the first direction is different from the second direction, and
        wherein the first layer is electrically insulated from the second layer,
    the capacitive sensor further comprising:
        an electronic driving module configured:
            to independently apply respective voltages on each of the first and second electrodes including at least one zero voltage on at least one of the first and second electrodes, and
            to measure electrical charges accumulated on each of the first and second electrodes,
        an information processing module configured for analyzing a spatial distribution of variations of the measured electrical charges for each one of the first and second electrodes by determining:
            information dependent on a coupling to ground of said one of the first and second electrodes if the voltage applied to said one of the first and second electrodes is not zero; or
            information independent of the coupling to ground if the voltage applied to said one of the first and second electrodes is zero and the voltage applied to at least one other electrode of the first and second electrodes is not zero;
        in order to detect, locate the presence, evaluate the floor surface and/or track the activity of an individual and/or an object.

2. The sensor as claimed in claim 1, wherein the first and second directions are substantially perpendicular to each other.

3. The sensor as claimed in claim 1, wherein the first and second layers extend in planes substantially parallel to each other.

4. The sensor as claimed in claim 1, comprising a display module comprising a control screen and coupled to the information processing module for generating an image on the control screen representative of the spatial position of the object and/or individual based on the spatial distribution of the measured charges for each of said electrodes.

5. The sensor as claimed in claim 1, wherein each electrode of the first and second layers is electrically insulated by a respective protective sleeve made at least partially of a polymer.

6. The sensor as claimed in claim 5, wherein each protective sleeve is held by a support having a perforated or airy structure.

7. The sensor as claimed in claim 6, wherein each support has at least one self-adhesive surface.

8. The sensor as claimed in claim 6, wherein each support comprises a centimeter mesh net made up at least partially of a material selected among fiberglass, polyester, polypropylene, polyethylene and polyamide.

9. The sensor as claimed in claim 8, wherein each electrode of the first and second layers is electrically insulated by a respective protective sleeve, and wherein, for each layer, the mesh net and the electrodes are assembled together by weaving of a warp yarn and weft yarn type, where said warp yarn and weft yarn are formed respectively by the sleeves of each electrode and the mesh net.

10. A floor structure for locating an object and/or an individual comprising a capacitive sensor, wherein the capacitive sensor comprises:
    a first layer comprising at least one first electrode extending in a first direction; and
    a second layer having at least one second electrode extending in a second direction;
    wherein the first direction is different from the second direction, and
    wherein the first layer is electrically insulated from the second layer,
    the capacitive sensor further comprising:
        an electronic driving module configured:
            to independently apply respective voltages on each of the first and second electrodes including at least one zero voltage on at least one of the first and second electrodes, and
            to measure electrical charges accumulated on each of the first and second electrodes,
        an information processing module configured for analyzing a spatial distribution of variations of the measured electrical charges for each one of the first and second electrodes by determining:
            information dependent on a coupling to ground of said one of the first and second electrodes if the voltage applied to said one of the first and second electrodes is not zero; or
            information independent of the coupling to ground if the voltage applied to said one of the first and second electrodes is zero and the voltage applied to at least one other electrode of the first and second electrodes is not zero;
        in order to detect, locate the presence, evaluate the floor surface and/or track the activity of an individual and/or an object.

11. The floor structure as claimed in claim 10, further comprising a bed layer and a smoothing compound layer, wherein the capacitive sensor is attached by adhesive on at least a portion of the upper surface of the bed layer.

12. The floor structure as claimed in claim 10, further comprising a bed layer and a smoothing compound layer, wherein the capacitive sensor is integrated in the smoothing compound layer by pouring the smoothing compound layer on the bed layer.

13. A method of manufacturing a floor structure, wherein the floor structure comprises a capacitive sensor for locating an object and/or an individual,
    the method of manufacturing comprising: positioning a first layer comprising at least one first electrode of the capacitive sensor such that said first electrode extends in a first fixed direction; and
    positioning a second layer (C2) comprising at least one second electrode of the capacitive sensor such that said second layer is electrically insulated from the first layer and said at least one second electrode extends in a second direction different from the first direction;

providing the capacitive sensor with an electronic driving module configured:
- to independently apply respective voltages on each of the first and second electrodes including at least one zero voltage on at least one of the first and second electrodes; and
- to measure electrical charges accumulated on each of the first and second electrodes, providing the capacitive sensor with an information processing module configured for analyzing a spatial distribution of variations of the measured electrical charges for each one of the first and second electrodes by determining:
- information dependent on a coupling to ground of said one of the first and second electrodes if the voltage applied to said one of the first and second electrodes is not zero; or
- information independent of the coupling to ground if the voltage applied to said one of the first and second electrodes is zero and the voltage applied to at least one other electrode of the first and second electrodes is not zero, in order to detect, locate the presence, evaluate the floor surface and/or track the activity of an individual and/or an object.

14. The method as claimed in claim 13, wherein, positioning the second layer comprises positioning the second layer such that the second direction is substantially perpendicular to the first direction.

\* \* \* \* \*